United States Patent [19]
Potnis et al.

[11] Patent Number: 5,614,283
[45] Date of Patent: Mar. 25, 1997

[54] ABSORBENT COMPOSITE WITH THREE-DIMENSIONAL FILM SURFACE FOR USE IN ABSORBENT DISPOSABLE PRODUCTS

[75] Inventors: Prasad S. Potnis, Terre Haute, Ind.; Michael A. Francis, Midlothian, Va.

[73] Assignee: Tredegar Industries, Richmond, Va.

[21] Appl. No.: 362,224

[22] Filed: Dec. 22, 1994

[51] Int. Cl.$^6$ ................................ A61F 13/46
[52] U.S. Cl. .............. 428/131; 428/74; 428/72; 428/73; 428/166; 428/178; 428/132; 428/137; 428/138; 428/913; 604/378; 604/385.1; 604/367
[58] Field of Search .................... 428/74, 72, 73, 428/166, 178, 132, 137, 138, 131, 913; 604/378, 385.1, 367

[56] References Cited

U.S. PATENT DOCUMENTS

| | | | |
|---|---|---|---|
| 3,929,135 | 12/1975 | Thompson | 128/287 |
| 4,360,021 | 11/1982 | Stima | 128/287 |
| 4,519,798 | 5/1985 | Dinius | 604/358 |
| 4,622,036 | 11/1986 | Goodrum | 604/367 |
| 4,994,053 | 2/1991 | Lang | 428/178 |
| 5,147,345 | 9/1992 | Young et al. | 604/378 |
| 5,151,091 | 9/1992 | Glaug et al. | 604/378 |
| 5,295,986 | 3/1994 | Zehner et al. | 604/385.1 |

OTHER PUBLICATIONS

Blood Solidification Systems—undated.
"Non Woven Industry" Dec. 1992 vol. 23, No. 12 p. 71.

*Primary Examiner*—William Watkins
*Attorney, Agent, or Firm*—Emch, Schaffer, Schaub & Porcello

[57] ABSTRACT

The absorbent composite comprises a three-dimensional formed film having a planar surface and three-dimensional surface defining a plurality of cavities or projections depending downwardly from a planar surface. A plurality of the cavities or projections or spaces defined by the cavities contain at least one type of absorbent material. The composite is useful in a fluid absorbent product having at least one liquid pervious layer and at least one liquid impervious layer where the absorbent composite is positioned between the liquid pervious layer and the liquid impervious layer.

41 Claims, 5 Drawing Sheets

ABSORBENT COMPOSITE WITH THREE-DIMENSIONAL FILM SURFACE FOR USE IN ABSORBENT DISPOSABLE PRODUCTS

TECHNICAL FIELD

The present invention relates to an absorbent composite, particularly to an absorbent composite which is useful in disposable personal care products.

BACKGROUND OF THE INVENTION

A wide variety of structures for disposable absorbent products are known in the art. These commercial absorbent products typically collect bodily fluids and include bandages, adult incontinence products, diapers and catamenial products. These disposable absorbent products include a liquid impervious backsheet or outer layer, an absorbent core layer and a liquid permeable topsheet or inner layer.

The absorbent core layer may comprise different types of material to absorb and store the solid, semi-solid and fluid masses. Customers have come to expect quality products in terms of retention of fluid. Leakage from any disposable product is regarded as totally unacceptable. Improving the performance of disposable products is continually pursued by the industry, both in terms of materials and structures of the disposable products.

The absorbent core layer comprises a predetermined amount of an absorbent material. Use of the absorbent materials reduces the overall thickness or bulk of the disposable product, yet provides the disposable product with an increase in absorbency. However, one concern with using the absorbent materials is that once the materials have absorbed a great amount of fluid, the absorbent material forms a somewhat impermeable mass which prevents the ready flow of liquids from one area of the disposable product to another. Therefore, while deposition of the fluid or semi-solid materials occurs generally in one area of the disposable product, there is not always full use of the remaining potential absorbency of the product in the areas which do not directly receive the liquid material.

Further, in certain cases, when an absorbent core comprises a highly absorbent material containing a hydrocolloid material, the hydrocolloid material becomes slippery and is unstable when swollen or wetted. The high absorbency material thus can migrate within the disposable product when wet. This causes the product to become unstable and to have areas of good absorbency and areas which do not efficiently absorb fluid materials. Further, this swelling or bunching of absorbent material may cause the disposable product to allow direct contact of the user's skin with the absorbent material. In certain instances, the absorbent material may be somewhat irritating to the skin and it is therefore desired to prevent contact of the absorbent materials with the skin.

Notwithstanding the existence of many types of disposable products, there is still a need for absorbent articles which permit more efficient use of the absorbent materials. Disposable articles which allow more efficient use of the absorbent material allow for the production of disposable products which require less absorbent material therein. These articles are less bulky, fit better and provide greater ease of wearing to the consumer. Other benefits include cost effectiveness and less recycling concerns with products having less absorbent material.

Therefore, it is the object of the present invention to provide disposable absorbent articles having improved fluid absorption and retention. It is a further object to provide articles which have an improved capability to remove fluid from the skin of the wearer.

It is still a further object to provide disposable absorbent products which more effectively utilize the characteristics of the absorbent materials which constitute part of the disposable product.

These advantages are obtained herein, as will be seen from the following disclosure.

DISCLOSURE OF THE INVENTION

The present invention relates to an absorbent composite and a disposable product containing such absorbent composite as a core layer therein. The disposable product comprises at least three general layers: at least one liquid acquisition inner layer; at least one absorbent composite core layer; and at least one liquid impervious or barrier outer layer. The liquid acquisition inner layer can comprise one or more layers of liquid pervious nonwoven or formed films and specialty films, including, for example, a tissue layer or a top or cover sheet. The liquid pervious inner layer quickly distributes and wicks the wetness away from the wearer's skin and into the absorbent composite layer where the liquid is absorbed and retained. The liquid impervious outer layer can comprise one or more layers of any suitable flexible film material, can be embossed or three-dimensional, and can have a plurality of microprotuberances to aid in providing the desired end use characteristics.

According to one embodiment of the present invention, the absorbent composite core layer comprises a three-dimensional formed film having a planar surface and a three-dimensional surface defining a plurality of cavities which depend from the planar surface. The plurality of cavities are at least partially filled with at least one type of an absorbent or reservoir entrapment material. In certain embodiments, the absorbent layer further comprises at least one type of liquid wicking material such as a fiber mass, bulk nonwoven material, absorbent coating material, or cellular foam material which aids in wicking the liquid from the liquid acquisition layer and into the absorbent materials.

According to another embodiment of the present invention, the absorbent layer comprises a three-dimensional formed film having a planar surface and a three-dimensional surface having a plurality of projections which depend from the planar surface. Each projection defines an aperture which has a first open end in the plane of the film and the second open end positioned in a spaced apart relationship from the first open end. The absorbent layer further comprises at least one type of absorbent material which is positioned in a plurality of spaces defined by the projections depending from the planar surface of the formed film. In certain embodiments, the absorbent layer further comprises at least one type of a liquid wicking material which is adjacent the second openings on the three-dimensional formed film. The liquid wicking materials aids in distributing the liquids to the absorbent material and to less saturated portions of the absorbent material.

One feature of the present invention is that an absorbent product having less bulk is produced.

Another feature is that the absorbent material can be retained at a desired location in the disposable product to provide maximum absorbency and fluid retention during use of the disposable product.

A further feature of the present invention is that any migration of the absorbent materials within the disposable product are minimized by use of the three-dimensional or formed film.

Further features will become more fully apparent in the following description of the embodiments of this invention and from the appended claims.

DETAILED DESCRIPTION OF THE PRESENT INVENTION

The present invention relates, in part, to an absorbent core layer comprising a three-dimensional formed film and at least one type of absorbent core material at least partially filling cavities or apertures within the three-dimensional structure of the formed film.

Figure 1:
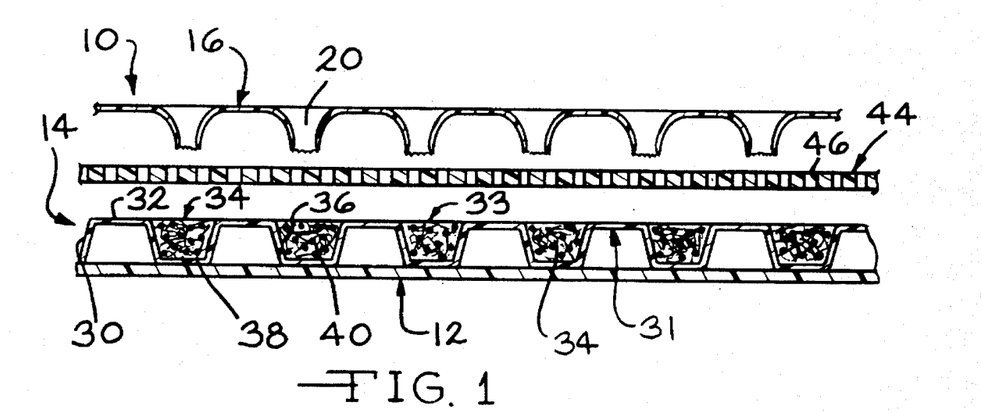
FIG. 1 is an exploded cross-sectional view of one embodiment of an absorbent product.

Referring now to the figures, an absorbent product 10 is shown herein which generally comprises three structural components as seen in the cross-sectional view in FIG. 1. The disposable product 10 comprises a liquid impervious backsheet or outer layer 12, an absorbent composite layer 14 and a liquid pervious topsheet or inner layer 16. It is to be understood that each of the layers 12, 14 and 16 can comprise one or more individual layers of materials. As can be seen in FIG. 1, the liquid impervious layer 12 is placed adjacent the absorbent core layer 14 which comprises one or more distinct components or layers as will be discussed herein. On top of the absorbent core layer is the liquid pervious layer 16. The topsheet layer 16 is positioned adjacent the wearer during use.

The liquid impervious layer 12 can be constructed of one or more layers of thin thermoplastic films comprising, for example, polyethylene, polypropylene or blends thereof or other flexible liquid impervious materials. For ease of illustration herein, the liquid impervious layer 12 is generally shown as being planar, however, it should be understood that the layer 12 can be embossed or have microprotuberances to aid in providing the desired texture and aesthetic appeal.

The liquid pervious layer 16 can comprise one or more layers of substantially porous materials which allow fluids to readily pass through the liquid pervious layer 16 and into the absorbent layer 14. In preferred embodiments, the liquid pervious layer 16 does not itself retain fluid such that there is a feeling of dryness when the disposable product 10 is adjacent the wearer's skin. In the absorbent product shown in FIG. 1, the liquid pervious layer 16 comprises a polymeric material having a plurality of apertures 20 which extend in a direction toward the absorbent layer 14. The apertures 20 in the liquid pervious layer 16 may be in the shape of tapered capillaries, slits, funnels, cylinders or other geometric or isometric shapes and may be varied in size and frequency to suit the particular viscosity, density, mass and flow rates of the fluid to be absorbed. The apertures 20 aid in fluid flow directly through the liquid pervious layer 16 into the absorbent layer 14.

The absorbent layer 14 comprises a three-dimensional formed film 30 and at least one type of absorbent material 40. The three-dimensional film 30 generally defines a three-dimensional surface 31 and a planar surface 32 having a plurality of cavities 34 defined by walls 36 and a base 38. Each cavity 34 extends in a direction away from the planar surface 32. Each cavity 34 has an opening 33 in the plane of the film 30 and an apex or base 38 which is remote from the plane of the film 30. Each cavity 34 is defined by walls 36 and the base 38. The walls 36 can extend either in a generally perpendicular direction from the planar surface 32 or can extend in a tapered, frustro-conical, or funneled direction as shown in FIG. 1. In certain embodiments, the diameter of the opening 33 is greater than the diameter of the base 38.

In the embodiment shown in FIG. 1, the cavities 34 are substantially filled with at least one type of absorbent material 40. It should be understood, however, that in other embodiments the absorbent material can almost fill the cavity or just be applied as a thin coating to the cavity. It is further understood that such variations in depth of the absorbent material are equally applicable to the other embodiments shown herein. The absorbent material 40 can comprise cellulose materials including fibers, cellular sponge or foam materials, super absorbent materials, such as hydrocolloidal materials and/or gel materials. Particularly useful absorbent materials are high absorbency gel-type materials which are generally capable of absorbing about 10 to about 50 times their weight in fluid. It is within the contemplated scope of the present invention that one or more of these types of absorbent materials are useful in the practice of the present invention. In particular, in certain embodiments, the absorbent material 40 can comprise a mixture of absorbent granular materials (AGM) and "fluff" comprising finely chopped cellulose fibers. It is optional, but advantageous in certain embodiments, to apply a suitable adhesive (not shown) to at least one surface of the three-dimensional film prior to filling the cavities 34 of the film with the absorbent material 40. The suitable adhesive adheres or bonds at least portions of the absorbent material to the formed film. The adhesive aids in keeping the absorbent material 40 within the cavities 34. In other embodiments, the adhesive can be applied or bonded to the three-dimensional film after the absorbent material 40 is contained within the cavities 34. It is to be understood that any suitable means to applying the adhesive, such as spraying and the like, can be used.

The three-dimensional formed film 30 can be a monolayer or coextruded multi-layer film. In preferred embodiments, the bulk of the film is preferably made from polyolefin resin blends such as low density polyethylene, linear medium density polyethylene, high density polyethylene, polypropylene and the like. The resin blends can be varied to control the wall thicknesses and resistance to compression, as well as the surface texture of the three-dimensional film 30.

The three-dimensional formed film 30 can be produced by using a cast film extrusion process or the combination of a cast film process combined with a fiber lamination process. The three-dimensional formed film can be produced such that the cavities 34 are distributed in various patterns. One particularly useful pattern or shape to the cavities 34 is a honeycomb shape. It is to be understood, however, that three-dimensional films having other patterns are also useful in the present invention. According to a preferred embodiment, the honeycomb three-dimensional film has sufficient stability to prevent the collapse of the three-dimensional structure during manufacturing of the absorbent product and during end use of the absorbent product. In one aspect of the present invention, a three-dimensional honeycomb formed film is produced using a metal screen (not shown) with hexagonal perforations. A thermoplastic resin material or blends thereof are extruded onto the screen. The thermoplastic material on the screen is subjected to vacuum in order to obtain a desired pattern on the thermoplastic material. In preferred embodiments, the resin blend and/or film thickness are optimumly adjusted to provide the desired stiffness of the cavity walls and yet also provide the desired softness of the texture of the resulting formed film. It is to be understood that the film can be perforated or non-perforated. The perforation of the film is achieved by an increase in the vacuum level, the required melt temperature, and the resin blends used in the formation of the film.

The dimensions of the formed film can be changed as required for the end product application. In certain embodiments, it has been found that a screen having hexagonal cells that are ⅛ inch in size, 115 mils deep, and made from welded metal ribbons that are 3.0 mils thick is especially useful in making a honeycomb formed film.

Other useful absorbent materials comprise nonwoven sponge materials or latex foams made by polymerizing latex or polymerizing monomers. The monomers can be mixed with precursors, such as sodium acrylates of AGM type materials and then polymerized inside the cavities. Yet another embodiment comprises using precursors of the AGM materials coated onto the film surface which are then polymerized. Yet, another embodiment comprises solution coating an absorbent material onto the film surface. It is to be understood that various types of absorbent and/or super absorbent materials are useful in the present invention and that all such materials are considered to be within the scope of this invention.

In certain embodiments, the amount of absorbent material 40 placed in the cavities 34 can be varied to provide optimum absorbency of the disposable product. For example, the areas of the disposable product which normally receive the bulk of the fluids can have more absorbent materials in the cavities of the absorbent layer than other, less used, areas of the disposable product.

In certain embodiments, the absorbent layer 14 further comprises a liquid wicking or distribution material 44 which is between the film 30 and the liquid pervious layer 16. The liquid distribution material 44 can also act to hold the absorbent material 40 in the cavities 34 of the formed film 30. It is contemplated that the material 44 can be suitably adhered to the liquid pervious layer 16 and/or the formed film 30 by any suitable means. The liquid distribution material 44 shown in FIG. 1 is a formed film having a plurality of perforations 46 such that fluid flows through the apertures 20 of the liquid pervious layer 16, through perforations 46 in the material 44, and contacts the absorbent material 40 in the film 30.

Figure 2:
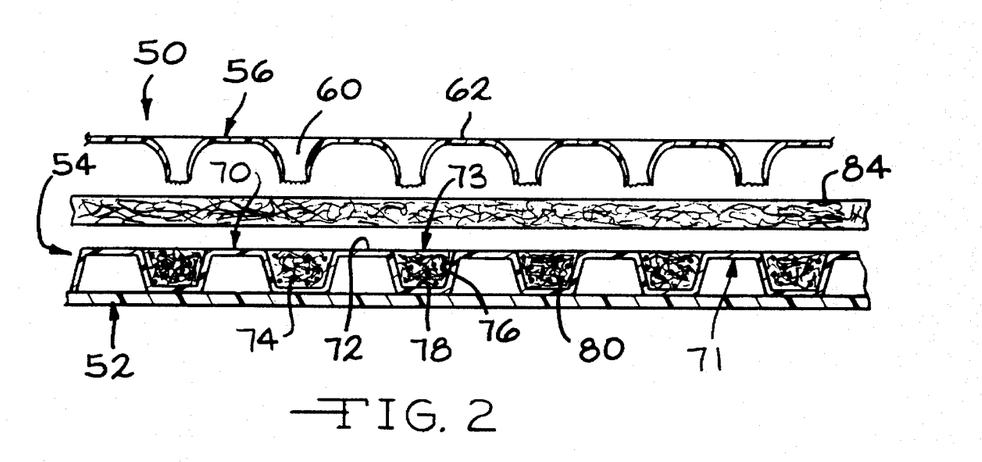
FIG. 2 is an exploded cross-sectional view of another embodiment of an absorbent product.

FIG. 2 shows a further different embodiment wherein an absorbent film composite 50 comprises a liquid impervious layer 52, an absorbent layer 54 and a liquid pervious layer 56. The liquid pervious layer 56 defines a plurality of apertures 60 which depend from a planar surface 62 of the layer 56 in a direction toward the absorbent layer 54.

The absorbent layer 54 comprises a three-dimensional formed film 70 and at least one type of absorbent material 80. The three-dimensional film 70 has a three-dimensional surface 71, a planar surface 72, and a plurality of cavities 74. Each cavity extends in a direction away from the planar surface 72. Each cavity has an opening 73 in the plane of the film 70 and a base 78 which is remote from the plane of the film 70. Each cavity 74 is defined by walls 76 and the base 78.

The cavities 74 are at least partially, and preferably completely filled with at least one type of absorbent material 80. The absorbent layer 54 further comprises a nonwoven liquid distribution material 84 which is positioned between the liquid pervious layer 56 and the formed film 70. The nonwoven material 84 can be comprised of melt blown, air-laid fibers or fibrous carded webs.

Figure 3:
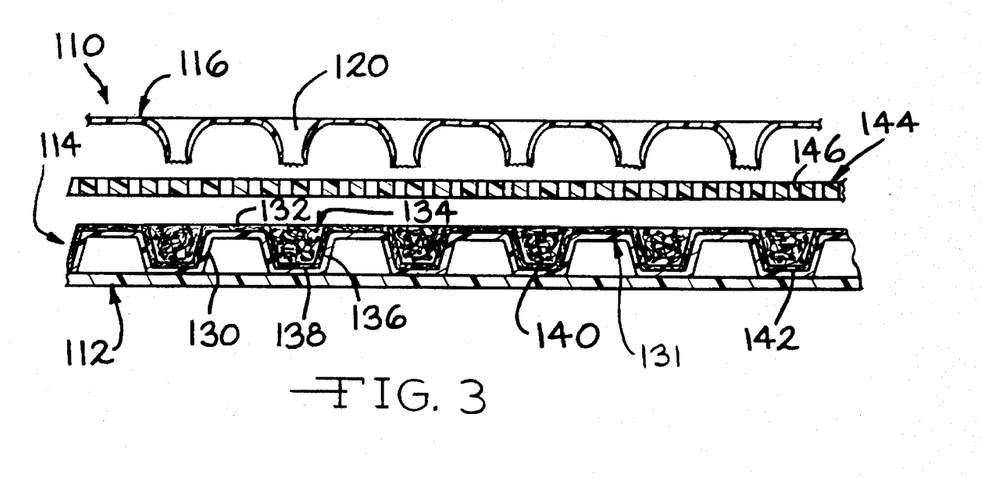
FIG. 3 is an exploded cross-sectional view of another embodiment of an absorbent product.

FIG. 3 shows a further embodiment wherein an absorbent product 110 comprises a liquid impervious layer 112, an absorbent core layer 114 and a liquid pervious layer 116. The liquid pervious layer 116 defines a plurality of apertures 120 which extend in a direction toward the absorbent layer 114. The absorbent layer 114 comprises a three-dimensional formed film 130 and a first absorbent material 140 and an additional absorbent material 142. The three-dimensional film 114 has a three-dimensional surface 131, a planar surface 132 and a plurality of cavities 134, each of which are defined by walls 136 and a base 138. In this embodiment, the additional absorbent material 142 is positioned adjacent at least a portion of the formed film 130 defined by the planar surfaces 132 and the cavities 134. The additional absorbent material 142 is positioned in at least a plurality of the cavities 134 defined by the walls 136 and bases 138 of the film 130. The additional absorbent material 142 substantially covers the planar surfaces 132, walls 136 and bases 138 of the formed film 130 and further improves the liquid acquisition properties of the absorbent layer 114. The additional absorbent materials useful in this embodiment can comprise absorbent materials as described above or can comprise at least one layer or fibrous web comprising polyolefins, polyesters, rayon or natural cellulosic fluff, super absorbent fibers and the like and have different stable lengths and diameters. The additional absorbent material 142 can be comprised of melt blown, air-laid fibers or lightly needled fibrous carded webs which can be bonded to the planar surface 132 and cavities 134 of the formed film 130. The mobility of the fibers comprising the additional absorbent material 142 allows the fibers to be drawn into the cavities 134 and cover the walls 136 of the film 130. In the embodiment shown in FIG. 3, the cavities 134 are at least partially, and preferably completely, lined with the additional absorbent material 142 and are at least partially, and preferably completely filled with at least one type of the absorbent material 140. It should be understood, however, that in other embodiments, the film 130 can comprise the cavities 134, at least partially lined with the additional absorbent material 142 and have no further absorbent material 140 (this embodiment not shown).

In certain embodiments, as shown in FIG. 3, the absorbent layer 114 further comprises a liquid wicking or distribution material 144 which is positioned between the liquid pervious layer 116 and the formed film 130. The material 144 contains a plurality of apertures 146 extending therethrough. In certain embodiments, the fibers comprising the additional absorbent material 142 can be drawn into the apertures 146 of the material 144 to aid in wicking the fluid away from the liquid pervious layer 116 and into the absorbent material 140.

Figure 4:
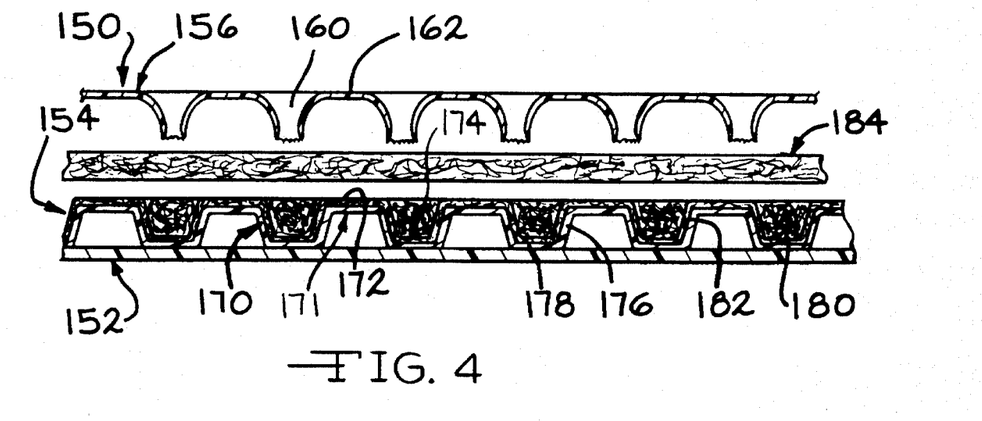
FIG. 4 is an exploded cross-sectional view of another embodiment of an absorbent product.

FIG. 4 shows another embodiment wherein an absorbent product 150 comprises a liquid impervious layer 152, an absorbent layer 154 and a liquid pervious layer 156. The liquid pervious layer 156 defines a planar surface 162 and a plurality of apertures 160 which extend from the planar surface 162 in a direction toward the absorbent layer 154.

The absorbent layer 154 comprises a three-dimensional formed film 170, a first absorbent material 180 and an additional absorbent material 182. The three-dimensional film 170 has a three-dimensional surface 171, a planar surface 172 and a plurality of cavities 174, each of which are defined by walls 176 and a base 178. The additional absorbent material 182 (similar to the additional absorbent material 142 in FIG. 3) is positioned adjacent the planar surfaces 172, walls 176 and bases 178 of the film 170. It should be understood, however, that in other embodiments, the film 130 can comprise the cavities 134, at least partially lined with just the additional absorbent material 182. In certain embodiments, as shown in FIG. 4, the cavities 174 are at least partially, and preferably completely, lined with the additional absorbent material 182 and are at least partially, and preferably completely, filled with at least one type of the absorbent material 180. In certain embodiments, as shown in FIG. 4, the absorbent layer 154 further comprises a nonwoven liquid distribution material 184 which is between the formed film 170 and the liquid pervious layer 156.

Figure 5:
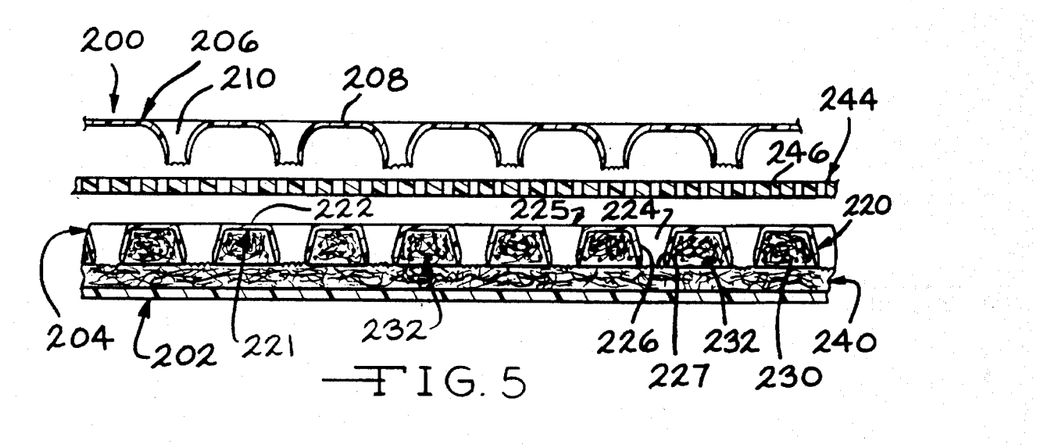
FIG. 5 is an exploded cross-sectional view of another embodiment of an absorbent product.

FIG. 5 shows a further embodiment wherein an absorbent product 200 comprises a liquid impervious layer 202, an absorbent layer 204 and a liquid pervious layer 206. The liquid pervious layer 206 defines a planar surface 208 and a plurality of apertures 210 which extend in a direction from the planar surface 208 toward the absorbent layer 204.

The absorbent layer 204 comprises a three-dimensional perforated film 220 and at least one type of absorbent material. The three-dimensional film 220 has a three-dimensional surface 221, a planar surface 222 and a plurality of perforations or apertures 224 which extend from the planar surface 222. The apertures 224 extend in a direction toward the outer layer 202 such that fluid readily passes through the apertures 224. Each aperture 224 is defined by walls 226. Each aperture 224 defines a first opening 225 in the plane of the film 220 and a second opening 227 remote from the plane of the film 220. The three-dimensional surface 221 is defined by the plurality of apertures 224 and by a plurality of spaces 232 which are areas between the apertures 224. Each space 232 is defined by the planar surface 222 and the walls 226 of the film 220. The absorbent core layer 204 further comprises at least one type of absorbent material 230 which is contained in a plurality of the spaces 232.

In the embodiment shown in FIG. 5, the absorbent layer 204 further comprises a first liquid distribution material 240 positioned between the film 220 and the outer layer 202. In preferred embodiments, the first liquid distribution material 240 comprises a nonwoven material. The first liquid distribution material 240 receives fluid through the apertures 224 in the film 220 and allows the liquid to be redistributed or absorbed into the absorbent material 230 in adjacent and surrounding spaces 232.

The absorbent layer 204 further comprises a second liquid distribution material 244 which is positioned between the liquid pervious layer 206 and the perforated film 220. The second liquid distribution material 244 is a formed film having a plurality of apertures 246 which allow fluids to pass from the liquid pervious layer 206 through the apertures 246 in the second liquid distribution material 244, through the apertures 224 in the perforated formed film 220, and into the first liquid distribution material 240 and into the absorbent material 230.

Figure 6:
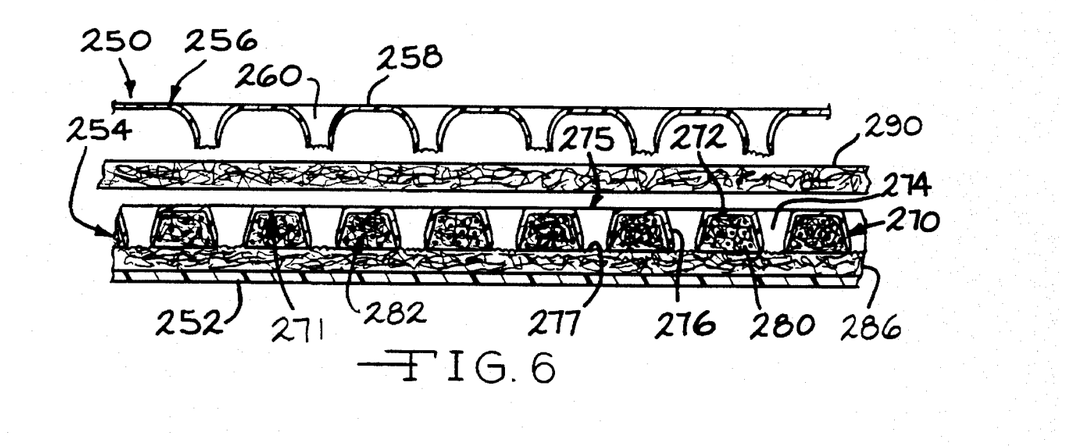
FIG. 6 is an exploded cross-sectional view of another embodiment of an absorbent product.

FIG. 6 shows a further embodiment wherein an absorbent product 250 comprises a liquid impervious outer layer 252, an absorbent layer 254 and a liquid pervious layer 256. The liquid pervious layer 256 defines a planar surface 258 and a plurality of apertures 260 which extend in a direction from the planar surface 258 toward the absorbent layer 254.

The absorbent layer 254 comprises a three-dimensional perforated film 270 and at least one type of absorbent material. The three-dimensional film 270 has a three-dimensional surface 271, a planar surface 272 and a plurality of perforations or apertures 274 which extend from the planar surface 272. The apertures 274 extend in a direction toward the outer layer 252 such that fluid readily passes through the apertures 274. Each aperture 274 is defined by walls 276. Each aperture 274 defines a first opening 275 in the plane of the film 270 and a second opening 277 remote from the plane of the film 270. The three-dimensional surface 271 is defined by the plurality of apertures 274 and by a plurality of spaces 282 which are areas between the apertures 274. Each space 282 is defined by the planar surface 272 and the walls 276 of the film 270. The absorbent core layer 254 further comprises at least one type of absorbent material 280 which is contained in a plurality of the spaces 282.

In the embodiment shown in FIG. 6, the absorbent layer 254 further comprises a first liquid distribution material 286 which is positioned between the perforated formed film 270 and the outer layer 252. In preferred embodiments, the first liquid distribution material 286 comprises a nonwoven material. The first liquid distribution material 286 receives fluid through the apertures 274 in the film 270 and allows the liquid to be redistributed or absorbed into the absorbent material 280 in adjacent and surrounding spaces 282.

The absorbent layer 254 further comprises a second liquid distribution material 290 which is positioned between the liquid pervious layer 256 and the perforated formed film 270. The second liquid distribution material 290 comprises a fibrous nonwoven material which aids in wicking the fluid away from the liquid pervious topsheet 256 and into the apertures 274 in the film 270 and into the first liquid distribution material 286 and the absorbent material 280.

Figure 7:
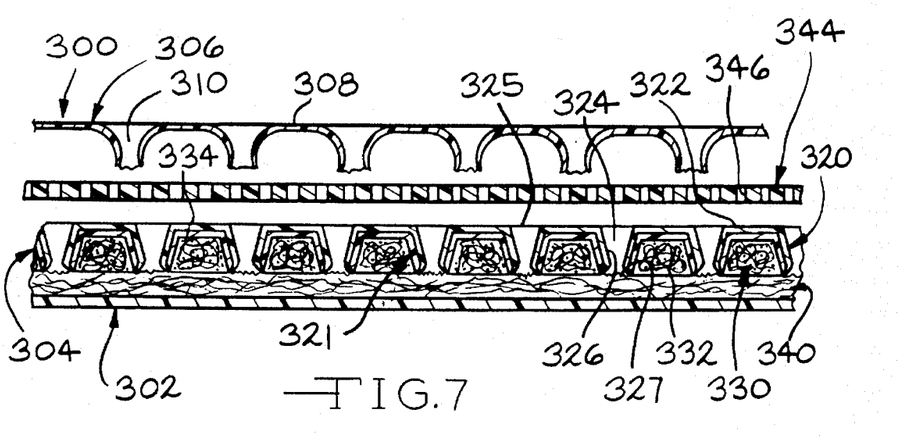
FIG. 7 is an exploded cross-sectional view of another embodiment of an absorbent product.

FIG. 7 shows a further embodiment, wherein absorbent product 300 comprises a liquid impervious layer 302, an absorbent layer 304 and a liquid pervious layer 306. The liquid pervious layer 306 defines a planar surface 308 and a plurality of apertures 310 which extend in a direction from the planar surface 308 toward the absorbent layer 304.

The absorbent layer 304 comprises a three-dimensional perforated film 320 and at least one type of absorbent materials. The three-dimensional film 320 has a three-dimensional surface 321, a planar surface 322 and a plurality of perforations or apertures 324 which extend from the planar surface 322. The apertures 324 extend in a direction toward the outer layer 302, such that fluid readily passes through the apertures 324. Each aperture 324 is defined by walls 326. Each aperture 324 defines a first opening 325 in the plane of the film 320 and a second opening 327 remote from the plane of the film 320. The three-dimensional surface 321 is defined by the plurality of apertures 324 and a by a plurality of spaces 332 which are areas between the apertures 324. Each space 332 is defined by the planar surface 322 and the walls 326 of the film 320. The absorbent layer 304 further comprises at least one type of absorbent material 330 which is contained in a plurality of spaces 332.

In the embodiment shown in FIG. 7, the absorbent core layer further comprises at least one additional absorbent material 334 which coats or is positioned adjacent at least a portion of the film 320 defined by the planar surfaces 322 and the apertures 324. The additional absorbent material 334 substantially coats the planar surface 322 and at least a plurality of the walls 326. The additional absorbent material 334 further improves the liquid acquisition properties of the absorbent layer 304. The additional absorbent materials useful in this embodiment can comprise absorbent materials as described above or can comprise at least one layer or web comprising polyolefins, polyesters, rayon or natural cellulosic fluff, super absorbent fibers and the like having different stable lengths and diameters. In certain embodiments, the additional absorbent material can be similar to the type of additional absorbent material discussed above in relation to FIGS. 3 and 4.

The absorbent layer 304 further comprises a first liquid distribution material 340 positioned between the film 320 and the outer layer 302. In preferred embodiments, the first liquid distribution material 340 comprises a nonwoven material. The first liquid distribution material 340 receives fluid through the apertures 324 and the film 320 and allows the liquid to be redistributed or absorbed into the absorbent material 330.

The absorbent layer 304 further comprises a second liquid distribution material 344 which is positioned between a liquid pervious layer 306 and the perforated film 320. The second liquid distribution material 344 is a formed film having a plurality of apertures 346 which allows fluid to be passed from the liquid pervious layer 306, to the apertures 346 in the second liquid distribution material 344, through the apertures 324 and the perforated formed film 320, and into the first liquid distribution material 340 and into the absorbent material 330.

Figure 8:
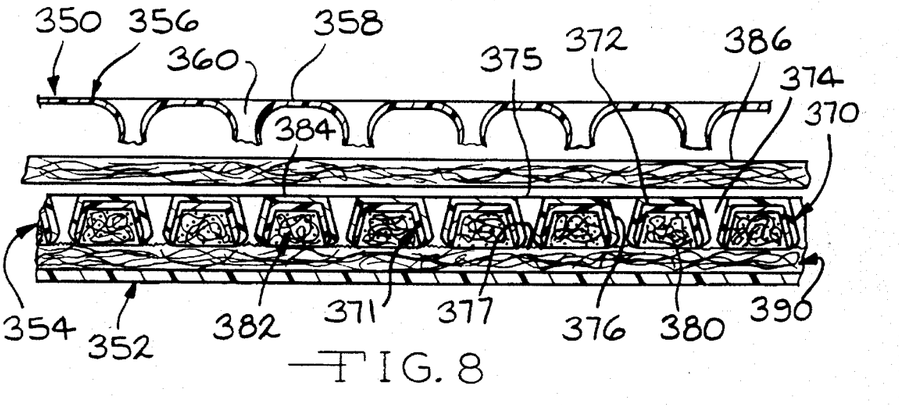
FIG. 8 is an exploded cross-sectional view of another embodiment of an absorbent product.

FIG. 8 shows a further embodiment, wherein an absorbent product 350 comprises a liquid impervious outer layer 352, an absorbent layer 354 and a liquid pervious layer 356. The liquid pervious layer 356 defines a planar surface 358 and a plurality of apertures 360 which extend in a direction from the planar surface 358 toward the absorbent layer 354. The absorbent layer 354 comprises a three-dimensional perforated film 370 and at least one type of absorbent material. The three-dimensional film 370 has a three-dimensional surface 371, a planar surface 372 and a plurality of perforations or apertures 374 which extend from the planar surface 372. The apertures 374 extend in a direction toward the outer layer 352 such that fluid readily passes through the apertures 374. Each aperture 374 is defined by walls 376. Each aperture 374 defines a first opening 375 in the plane of the film 370 and a second opening 377 remote from the plane of the film 370. The three-dimensional surface 371 is defined by the plurality of apertures 374 and by a plurality of spaces 382 which are areas between the apertures 374. Each space 382 is defined by the planar surface 372 and the walls 376 of the film 370. The absorbent core 354 further comprises at least one type of absorbent material 380 which is contained in a plurality of spaces 382.

In the embodiment shown in FIG. 8, the absorbent layer 354 further comprises a first liquid distribution material 386 which is positioned between the perforated formed film 370 and the outer layer 352. In preferred embodiments, the first liquid distribution material 386 comprises a nonwoven material. The first liquid distribution material 386 receives fluid through the apertures 374 in the film 370 and allows the liquid to be redistributed or absorbed into the absorbent material 380.

The absorbent core layer further comprises at least one additional absorbent material 384 which coats or is positioned adjacent at least a portion of the film 370 defined by the planar surfaces 372 and apertures 374. The additional absorbent material 384 coats at least a plurality of the walls 376. The additional absorbent material 384 substantially covers the planar surfaces 372 and the walls 376 and further improves the liquid acquisition properties of the absorbent layer 354. The additional absorbent materials useful in this embodiment can comprise absorbent materials as described above, or can comprise at least one layer or web comprising polyolefins, polyesters, rayons or natural cellulosic fluff and the like having different stable lengths and diameters. Alternatively, the additional absorbent material can be similar to the additional absorbent material discussed in relation to FIGS. 3 and 4.

The absorbent layer 354 further comprises a second liquid distribution material 390 which is positioned between the liquid pervious layer 356 and the perforated formed film 370. The second liquid distribution material 390 comprises a fibrous nonwoven material which aids in wicking the fluid away from the liquid pervious topsheet 356 and into the apertures 374 and the film 370, and into the first liquid distribution material 386 and the absorbent material 380.

Figure 9:
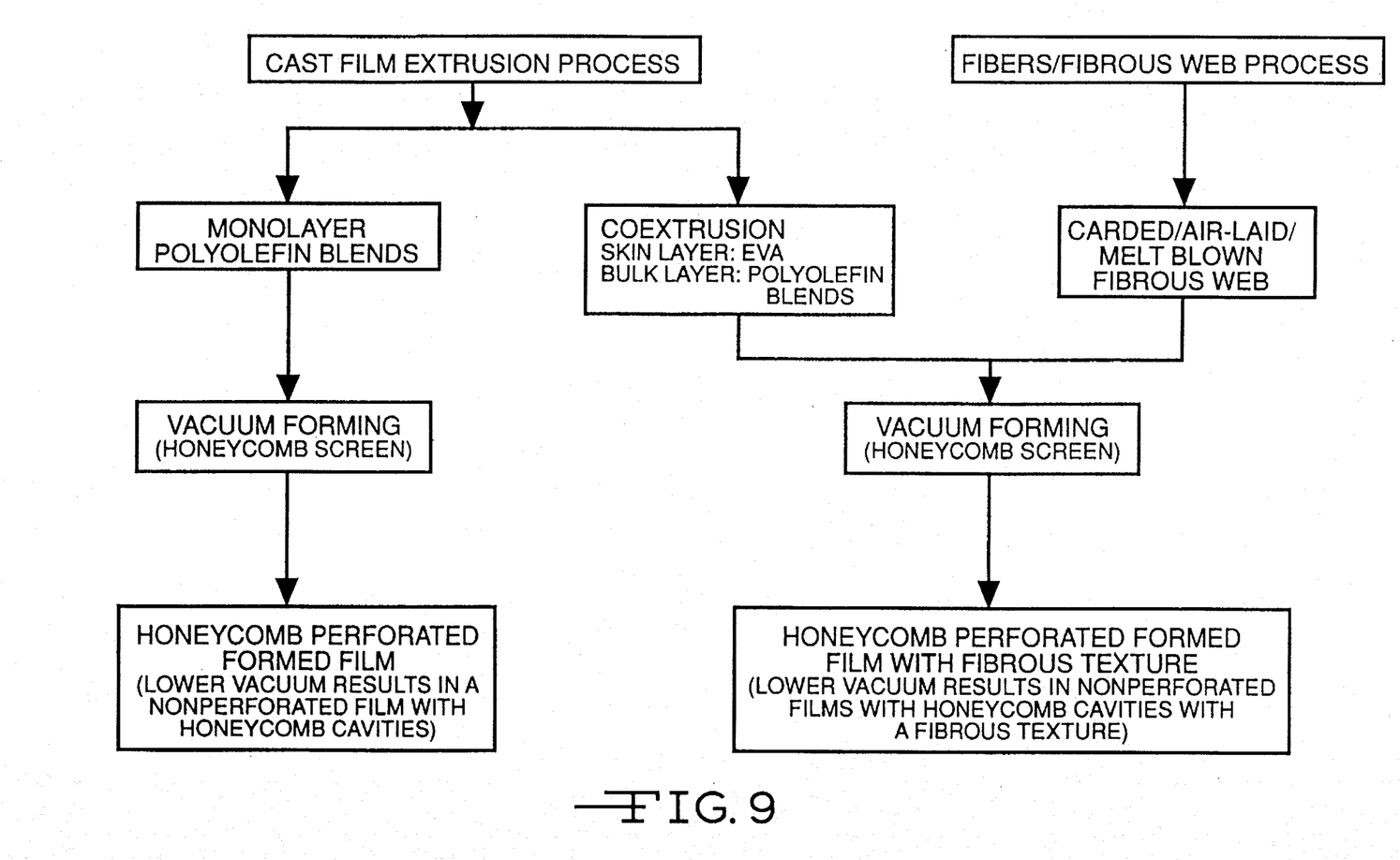
FIG. 9 is a schematic diagram showing processes for making perforated or non-perforated three-dimensional formed films.

FIG. 9 is a schematic diagram showing two methods for producing three-dimensional perforated and/or non-perforated formed films with a fibrous texture for use in absorbent disposable products. The absorbent layer can be laminated with the fibrous material and can be formed by drawing fibers along with the extruded melt resin to obtain the perforated formed film with a fibrous texture. The cast film extrusion process can produce a monolayer polyolefin blend which is vacuum formed using a screen in combination with a vacuum level which perforates the film. In alternative embodiments, use of a lower vacuum pressure results in a non-perforated film with three-dimensional cavities.

Certain embodiments can comprise a coextruded film, having a top layer and a bottom layer. The top layer can comprise a type of material (for example ethylene vinyl acetate) which assists in bonding of laminating fibers and fibrous webs to the planar surface of the film and along the walls of the cavities and/or apertures in the film. The bottom layer can comprise, for example, a polyolefin blend material. Fibrous webs or fibers including carded, or air-laid or melt blown nonwoven webs can be laminated with the three-dimensional formed film. The fibrous webs are dispensed onto a vacuum forming apparatus having a perforated screen. The perforated formed film with fibrous textures are produced by drawing sufficient air across the vacuum to perforate the film. The use of a lower vacuum pressure results in non-perforated film having a plurality of cavities and a fibrous texture on one surface of the formed film.

Absorbent film composites were made using non-perforated formed film wherein absorbent material powders (designated as absorbent gel materials-AGM) were distributed into the cavities of the formed film. In one example, a combination of AGM powder and cellulose fluff or fibers was used to fill the cavities. Four different types of composites were made, all of which had an AGM-filled formed film as the bottom layer and also had: (1) a top layer of an apertured patterned formed film; (2) a top layer carded nonwoven material; (3) a top layer of an apertured patterned formed film and a middle layer of a bulky air-laid chemically bonded nonwoven; and (4) a top layer of an apertured patterned formed film over a honeycomb film with cavities filled with fluff and AGM materials. It is contemplated that, in certain embodiments, an adhesive type material can be applied onto the cavities to help hold the absorbent materials in place in the cavities. In embodiments where adhesives may partially cover the absorbent material particles, it is contemplated that a formed film having a skin layer comprising, for example, EVA or hot melt adhesive layer, can be applied to the planar side of the formed film. The adhesive layer can be thermally or ultrasonically activated after the cavities are filled with the absorbent material particles such that the absorbent materials bond to the film.

In other embodiments, controlled quantities of the absorbent material can be transferred into the cavities using a spray system or alternatively an engraved roll applicator. Any extra absorbent material can be recovered and recycled. The formed film perforated layers provided sufficient liquid acquisition and distribution and also prevented post-absorption swollen absorbent materials from leaking out of the composite. In various embodiments, a layer of bulked nonwoven material (3.0 oz/sq.) was provided which covered the layers of apertured formed films. The nonwoven layer prevents liquid leakage and also provides for a greater residence time, thereby increasing the efficiency of the absorbent materials.

In one test, it was observed that the position of the nonwoven (reservoir) layer resulted in absorption and retention of 300 ml of water by a composite 300 sq.cm. in surface area and a thickness of about 1 cm.

In other embodiments, the nonwoven layer can be replaced with a hydrophilic polyethylene based open celled foam or sponge layer which also functions as a reservoir medium to immobilize and hold a liquid before being absorbed by the super absorbent particles. Still another embodiment provides a liquid reservoir medium by filling the cavities with a mixture of fibers and absorbent material.

Yet another embodiment comprises using a foam mixture of a sodium salt of the acrylic acid (plus catalyst) and hydrophilic particles (including surfactants) and polymerizing this foam mixture in the cavities of the formed film using heat or radiation energy to obtain a cellular hydrophilic medium that contains the super absorbent materials. The cellular nature of the formed film retains any liquids until the super absorbent material absorbs the liquid and swells inside the cavities. It is to be understood that the dimensions of the cavities can be varied as required to contain a desired amount of absorbent material required for the optimum fluid storage capacity.

In yet another embodiment, a combination of a melt blown or air-laid/carded web nonwoven process is utilized along with a vacuum film forming process having a honeycomb screen. The product is a fibrous three-dimensional film material with cavities. Still another embodiment comprises using at least two types of absorbent materials to provide a quick wicking away action. One material can have a fast rate of absorption and a lower absorbent capacity which is used together with another absorbent material having a higher absorbent capacity, but lower rate of absorption.

In various embodiments, as shown in FIGS. 1, 3 and 7, a liquid distribution material comprises a perforated film material such as polyolefins, including polyethylene or ethylene vinyl acetate, which is bonded onto the planar side of the formed film. The liquid distribution material also firmly holds the absorbent materials and fiber mixture to the film surface inside the cavities and prevents the absorbent material from being displaced from the cavities. In various other embodiments as shown in FIGS. 2, 4 6 and 8, it is useful to use a surfactant treated polyethylene nonwoven material rather than a formed film to aid in liquid distribution. In other embodiments, a polyethylene nonwoven material can be air-laid on the film to aid in liquid distribution and retention.

It is contemplated that the liquid distribution material can be laminated to the planar side of the film after the cavities are at least partially filled with the absorbent materials.

EXAMPLE I.

An absorbent core made with the honeycomb film with cavities filled with a mixture of AGM and fluff particles and cover sheets of an apertured patterned formed film was tested. The absorbent core of surface area 56.25 sq.in. or 362 sq.cm. and ⅛ in. thick was tested with up to 150 ml of warm water. There was almost instantaneous absorption of the fluid. No water leaked or exited the absorbent core even on turning it upside down after two to three minutes. This was possible without any nonwoven layer in the core. The absorbent core absorbed water up to 200 ml and did not leak.

EXAMPLE II

An absorbent core was made with a honeycomb film with cavities filled with a mixture of AGM and fluff fibers. This was covered with layers of formed film. The absorbent core exhibited excellent liquid acquisition performance. The layers of formed film also held the particles of water swollen AGM in the core. The core was tested using two quantities of AGM particles and two sizes (core volumes).

An apparatus used to evaluate the Liquid Run Off performance of formed films was used to dose the required quantities of synthetic urine. In this core testing, 100 ml of synthetic urine was dosed at a rate of 5 ml per second by placing the dosing tube 0.5 in. directly over the center of the absorbent core. Upon completion of the dosing of the 100 ml of synthetic urine, a 25 second waiting period was used, after which the core was tilted and then overturned to check for liquid leakage. The liquid that leaked during the tilting was collected in a beaker and measured with a graduated measuring cylinder.

Core performance evaluation was carried out in the following cases:

In the first case, the core was made with formed films that were 7.0 in. by 7.0 in. (49 sq.in.) with a total thickness of 0.1 to 0.105 in. to result in a core volume of about 80 to 85 mi. In this case, 2.0 grams of AGM and about 3.0 grams of Fluff was filled in the honeycomb cavities. The core was sealed on all four sides to prevent leakage from the sides.

In the second case, the core was made with formed films that were 8.0 in. by 8.0 in. with a total thickness of 0.1 to 0.105 in. to result in a core volume of about 104 to 110 ml. In this case, 4.0 grams of AGM and about 3.0 grams of Fluff was filled in the honeycomb cavities. The core was sealed on all four sides to prevent leakage from the sides.

In the third case, the core was made with formed films that were 8.0 in. by 8.0 in. and a layer of 8.0 by 8.0 in. of a dense needled punched nonwoven material was placed between the honeycomb film and the covering layers of formed films. In this case, the cavities were filled with about 4.0 grams of AGM and no Fluff.

In each case, a set of five samples were tested by using the method given above. The cores exhibited excellent liquid acquisition at the dosing rate of 5.0 ml of synthetic urine per second.

In the first case for core volume of 80 to 85 ml (7"×7" formed films) the use of 2.0 grams of AGM and 3.0 grams of Fluff resulted in the absorption of 85 ml of synthetic urine after the 25 seconds waiting period. The rest of the liquid leaked out when the core was tilted and later overturned. The amount of liquid that was not absorbed was collected and measured with a graduated cylinder.

In the second case for a core volume of 104 to 110 ml (8"×8" formed films) the use of 4.0 grams of AGM and 3.0 grams of Fluff resulted in the absorption of 100 ml of synthetic urine used in the test after the 25 seconds waiting period. No liquid leaked out when the core was tiled and later overturned.

In both the first and second case, more liquid was absorbed if a waiting period of longer than 25 seconds was used to test the core. In previous tests, cores with less than 2.0 grams of AGM required a longer time to absorb 100 ml of liquid. In an attempt to increase the amount of liquid absorbed in the core in a short time (25 seconds or less) a layer of dense needle punches nonwoven was used between the layers of formed films and the honeycomb formed film. Surprisingly, this resulted in absorbing a lower amount of liquid in the specified time. This was attributed to the fact that the dense layer of nonwoven retained the liquid and did not transfer it to the AGM in the cavities. In the past when a nonwoven of a lower density was used, more liquid was absorbed by the core, although the time required in that case was about five minutes. This showed that the core made with honeycomb cavities filled with AGM and fibers without the nonwoven layer exhibited better liquid acquisition and absorption performance when tested with 100 ml of synthetic urine and a waiting period of 25 seconds after the completion of the liquid dosing onto the core.

The performance of the absorbent core is not only dependent on its capability to store the liquid until the liquid is absorbed by the absorbent material, but also the proper and rapid transfer of the liquid from the storage layer into the cavities filled with the absorbent material. In the case of the core with cavities filled with absorbent material and fibers, the fibers help store and efficiently transfer the liquid to the absorbent material in its vicinity resulting in rapid absorption of the transferred liquid. The capacity of the core can be enhanced by increasing the dimensions of the cavities to contain increased quantities of absorbent material and fibers to be able to absorb more liquid at a potentially faster rate.

In other embodiments, fibrous webs made up of loose short fibers are melt-bonded to the honeycomb cavities during film formation. Such honeycomb films have a skin layer of EVA on the planar side to assist in the bonding of the fibers to the planar side of the film. On filling the honeycomb cavities with the absorbent material particles, the layers of formed film are laminated to the honeycomb cavities using an adhesive spraying system. A fibrous web lay-up with a melt blown nonwoven system on the planar side of the honeycomb film or even the use of a formed cover layer with a melt blown fibrous layer sprayed on its apertured side is also useful.

While the present invention has been described in detail with respect to specific embodiments thereof, it will be appreciated that those skilled in the art may readily conceive alterations, to variations of and in equivalence to those embodiments. The scope of the present invention should therefore be assessed by the appended claims and the equivalents thereto.

We claim:

1. An absorbent composite comprising a three-dimensional fluid impermeable, formed film having a planar surface and a three-dimensional surface which defines a plurality of cavities depending downwardly from the planar surface, the cavities providing dimensional stability to the formed film to substantially prevent collapse of the absorbent structure, wherein a plurality of the cavities contain at least one type of absorbent material; and at least one fluid distribution material positioned adjacent the planar surface of the formed film.

2. The absorbent composite of claim 1, wherein the absorbent material comprises at least one hydrogel material, cellulose material or mixtures thereof.

3. The absorbent composition of claim 1, wherein the liquid distribution material comprises a perforated formed film.

4. The absorbent composite of claim 1, wherein the liquid distribution material comprises a nonwoven fibrous material.

5. The absorbent composite of claim 1, wherein the absorbent composite further comprises at least one additional type of absorbent material positioned adjacent the planar surface and within at least a plurality of the cavities of the formed film.

6. The absorbent composite of claim 5, wherein the additional absorbent material comprises a coating of absorbent material on the planar surface and within the cavities of the formed film.

7. The absorbent composite of claim 6, wherein the additional absorbent material comprises a fibrous web.

8. The absorbent composite of claim 1, wherein at least a portion the cavities of the formed film are distributed in a pattern.

9. The absorbent composite of claim 8, wherein the cavities of the formed film are present in a honeycomb pattern.

10. The absorbent composite of claim 1, wherein a plurality of the cavities have a frustro-conical shape.

11. The absorbent composite of claim 1, wherein the cavities define an opening in the plane of the film and an apex remote from the plane of the film.

12. The absorbent composite of claim 11, wherein the cavities are defined by walls which taper from the opening toward the apex such that each opening in the plane of the film has a first cross-section or diameter and each apex has a second cross-section or diameter smaller than the cross-section or diameter of the opening.

13. The absorbent composite of claim 1, wherein the three-dimensional formed film is a monolayer film comprising at least one polyolefin resin.

14. The absorbent composite of claim 1, wherein the three-dimensional formed film comprises a coextruded film having a top layer, and a lower layer, the lower layer comprising at least one polyolefin resins.

15. The absorbent film composite of claim 14, wherein the top layer comprises ethylene vinyl acetate.

16. The absorbent composite of claim 1, wherein the absorbent material is adhered to the formed film with a suitable adhesive.

17. The absorbent composite of claim 1, wherein the absorbent material is adhered to the formed film by applying heat, radiant or ultrasonic energy to the absorbent composite.

18. The absorbent composite of claim 16, wherein the absorbent core is adhered to the formed film by applying the suitable adhesive to a plurality of the cavities prior to substantially filling the cavities with the absorbent material.

19. The absorbent composite of claim 16, wherein the absorbent material is adhered to the formed film by applying the suitable adhesive to a plurality of the cavities after substantially filling the cavities with the absorbent material.

20. A fluid absorbent article comprising at least one liquid pervious layer, at least one liquid impervious layer, and at least one absorbent layer comprising the absorbent composite of claim 1 positioned between the liquid pervious layer and the liquid impervious layer.

21. An absorbent composite comprising a three-dimensional perforated formed film having a planar surface, and a three-dimensional surface which defines a plurality of projections depending from the planar surface, each projection defining an aperture which has a first, open end in the plane of the film and a second, open end positioned in a spaced apart relationship from the first open end, the planar surface of the film and each projection further defining a space;

at least one type of absorbent material positioned in a plurality of the spaces defined between the projections depending from the planar surface of the formed film, the absorbent material being in substantial communication in the spaces defined between the projection; and, at least one liquid distribution material positioned adjacent the second open ends of the apertures defined by the projections depending from the planar surface of the three-dimensional formed film.

22. The absorbent composite of claim 21, wherein the absorbent material comprises at least one hydrogel material, cellulose material or mixtures thereof.

23. The absorbent composite of claim 21, wherein the liquid distribution material comprises a nonwoven fibrous material.

24. The absorbent composite of claim 21 further comprising at least one further liquid distribution layer positioned adjacent the planar surface of the perforated formed film.

25. The absorbent material of claim 24, wherein the further liquid distribution layer comprises a perforated formed film.

26. The absorbent material of claim 24, wherein the further liquid distribution layer comprises a nonwoven fibrous material.

27. The absorbent composite of claim 21, wherein the absorbent composite further comprises at least one additional type of absorbent material positioned within a plurality of the spaces defined by the projections of the formed film.

28. The absorbent composite of claim 27, wherein the additional absorbent material comprises a coating of absorbent material on the planar surface and the projections of the formed film.

29. The absorbent composite of claim 28, wherein the additional absorbent material comprises a fibrous web.

30. The absorbent composite of claim 21, wherein at least a portion of the apertures of the formed film are distributed in a pattern.

31. The absorbent composite of claim 30, wherein the apertures of the formed film are present in a honeycomb pattern.

32. The absorbent composite of claim 21, wherein a plurality of apertures have a frustro-conical shape.

33. The absorbent composite of claim 21, wherein the apertures are defined by the projections which taper from the first open end toward the second open end.

34. The absorbent composite of claim 21, wherein the formed film is a monolayer comprising at least one polyolefin resin.

35. The absorbent composite of claim 21, wherein the formed film comprises a coextruded film having a top layer and a lower layer, the lower layer comprising at least one polyolefin resin.

36. The absorbent composite of claim 35, wherein the top layer comprises ethylene vinyl acetate.

37. The absorbent composite of claim 21, wherein the absorbent material is adhered to the formed film with a suitable adhesive.

38. The absorbent composite of claim 25, wherein the absorbent material is adhered to the formed film by applying heat, radiant or ultrasonic energy to the absorbent composite.

39. The absorbent composite of claim 37, wherein the absorbent core is adhered to the formed film by applying the suitable adhesive to a plurality of the cavities prior to substantially filling the cavities with the absorbent material.

40. The absorbent composite of claim 37, wherein the absorbent core is adhered to the formed film by applying the suitable adhesive to a plurality of the cavities after substantially filling the cavities with the absorbent material.

41. A fluid absorbent article comprising at least one liquid pervious layer, at least one liquid impervious layer and at least one absorbent layer comprising the absorbent composite of claim 21 positioned between the liquid pervious layer and the liquid impervious layer.

* * * * *